United States Patent [19]

Sivash

[11] 4,077,070
[45] * Mar. 7, 1978

[54] ARTIFICIAL HIP JOINT

[76] Inventor: Konstantin Mitrofanovich Sivash, ulitsa Bolshaya Pirogovskaya, 37/43-A, kv. 49, Moscow, U.S.S.R.

[*] Notice: The portion of the term of this patent subsequent to Jun. 28, 1991, has been disclaimed.

[21] Appl. No.: 605,822

[22] Filed: Aug. 19, 1975

Related U.S. Application Data

[60] Division of Ser. No. 414,431, Nov. 9, 1973, Pat. No. 3,943,576, which is a division of Ser. No. 189,261, Oct. 14, 1971, Pat. No. 3,820,167, which is a continuation-in-part of Ser. No. 737,910, Jun. 18, 1968, abandoned.

[51] Int. Cl.$^2$ .............................................. A61F 1/24
[52] U.S. Cl. ................................. 3/1.912; 128/92 C
[58] Field of Search .............................. 3/1.9–1.913, 3/1; 128/92 C, 92 CA

[56] References Cited

U.S. PATENT DOCUMENTS 3,820,167  6/1974  Sivash ................................... 3/1.912

FOREIGN PATENT DOCUMENTS

| 1,047,640 | 7/1953 | France | 128/92 C |
| 124,585 | 3/1959 | U.S.S.R. | 128/92 C |
| 278,022 | 4/1970 | U.S.S.R. | 3/1.912 |

Primary Examiner—Ronald L. Frinks
Attorney, Agent, or Firm—Haseltine, Lake & Waters

[57] ABSTRACT

An artificial hip joint is provided having an acetabulum prosthesis of the cotyloid cavity defining a socket and having a plurality of blades extending outwardly away from the socket for engaging the prepared wall of the cotyloid cavity. A prosthesis of the head of the femur is movably interconnected with the acetabulum prosthesis and includes a pin to be driven into the bone-marrow channel of the femur, a curved neck integral with the pin, and a hip ball fixedly positioned on the neck and movably located within the socket, the socket enveloping more than one-half of the hip ball to prevent withdrawal of the hip ball from the socket.

6 Claims, 6 Drawing Figures

ARTIFICIAL HIP JOINT

This application is a division of Ser. No. 414,431, filed Nov. 9, 1973 now issued as U.S. Pat. No. 3,943,576 which in turn is a division of Ser. No. 189,261, filed Oct. 14, 1971, now issued as U.S. Pat. No. 3,820,167 and which in turn is a continuation-in-part of Ser. No. 737,910, filed June 18, 1968 now abandoned.

The present invention relates to artificial joints and more particularly to an artificial hip joint.

Numerous types of artificial hip joints have been developed and are being used. These joints have been made with various types of materials in attempts to provide both a strong joint and one that will not be unduly corroded by the body environment. Various styles and arrangements of artificial hip joints having an artificial acetabulum articulately connected to an artificial caput femoris have been developed; however, use of these joints has made evident inherent disadvantages due to the shapes of the hips and to the materials used. Bone growth stimulated by the mechanical irritation of the artificial joints has also resulted in partial immobilization of the joints with a concomitant gradual increase of painful sensations.

Accordingly, it is an object of the present invention to provide an artificial hip joint that will provide all of the functions inherent in a normal human hip joint and which possesses great strength and service life.

Another object is to provide an artificial hip joint that is light in weight.

A further object of the invention is the provision of an artificial hip joint that avoids immobilization due to undesirable fibrous and bone growths around the joint.

Still another object is to provide an artificial hip joint which advantageously utilizes the normally undesirable fibrous and bone growths to assist in holding the joint in position within the body.

Still another object of the present invention is the provision of an artificial hip joint which is relatively simple and inexpensive to manufacture and which is relatively easy to insert into the body.

Additional objects and advantages of the invention will be set forth in part in the description which follows, and in part will be obvious from the description, or may be learned by practice of the invention. The objects and advantages are realized and attained by the instrumentalities and combinations particularly pointed out in the appended claims.

To achieve these and other objects the present invention provides an artificial hip joint having an acetabulum prosthesis of the cotyloid cavity defining a socket and having a plurality of blades extending outwardly from the socket for engaging the prepared wall of the cotyloid cavity, and a prosthesis of the head of the femur movably interconnected with the acetabulum prosthesis and including a pin to be driven into the bone-marrow channel of the femur, a curved neck integral with the pin, and a hip ball positioned on the neck and movably located within the socket, the socket enveloping more than one-half of the hip ball to prevent withdrawal of the hip ball from the socket.

As here embodied, predetermined ones of the acetabulum blades have holes therein for enabling growth of bone tissue through the holes and around the blades for holding the acetabulum prosthesis in position within the body. In addition, the acetabulum prosthesis preferably includes two inserts, each of the inserts having a surface area for contacting the hip ball over more than one-fouth of the spherical surface area of the hip ball. The acetabulum prosthesis preferably has an aperture therein and each of the inserts preferably includes projections riveted through the acetabulum aperture for holding the inserts in position.

As here embodied, the artificial hip joint also preferably includes an enlarged shoulder integral with and between the pin and the neck, the neck having a base joined at the shoulder and eccentrically positioned with respect to the central axis of the pin. Preferably, a portion of the neck extends upwardly from the shoulder and in a continuous manner from a side portion of the shoulder.

It is to be understood, of course, that both the foregoing general description and the following detailed description are explanatory only and are not restrictive of the invention.

The accompanying drawings, which are incorporated in and constitute a part of the specification, illustrate a preferred embodiment of the invention, and together with the description, serve to explain the principles of the invention.

Figure 1:
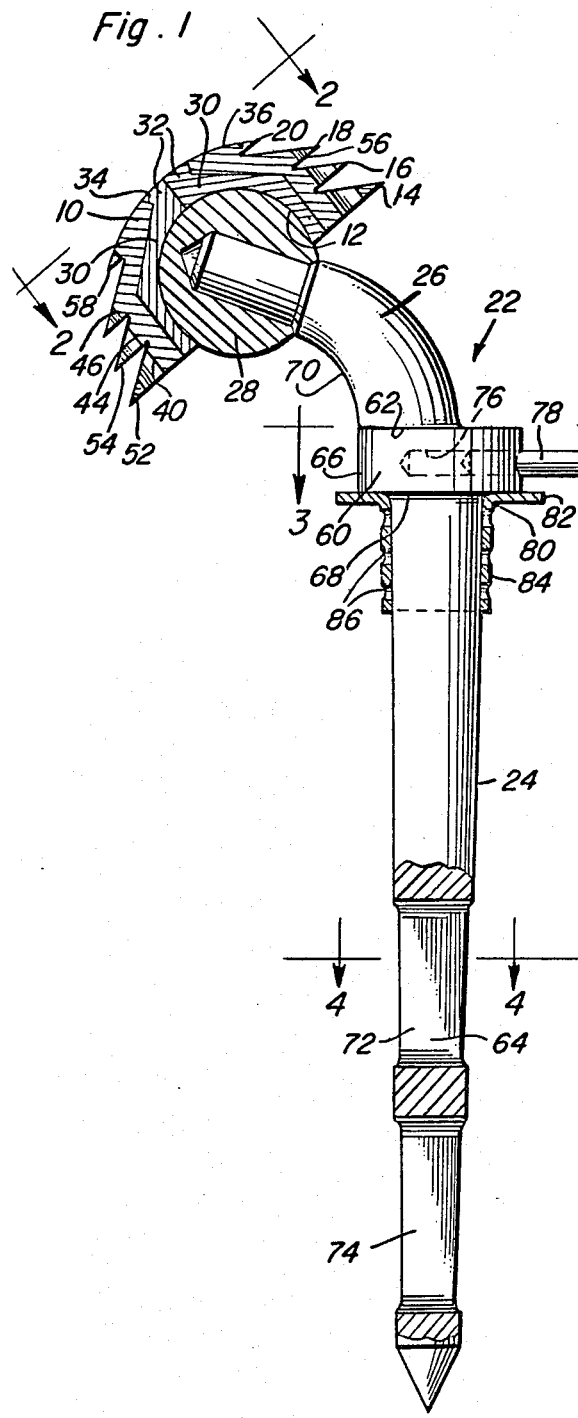
FIG. 1 is an elevation view, partially in section, of the artificial hip joint of this invention.
Figure 2:
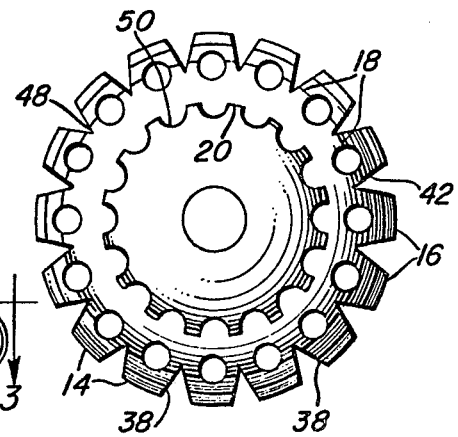
FIG. 2 is a view taken on the line 2—2 of FIG. 1 and looking in the direction of the arrows.
Figure 3:
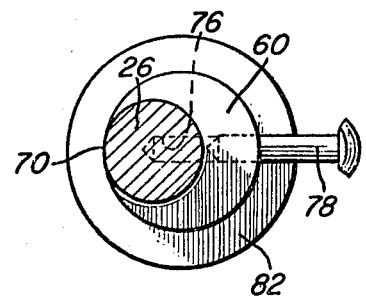
FIG. 3 is a view taken on the line 3—3 of FIG. 1 and looking in the direction of the arrows.
Figure 4:
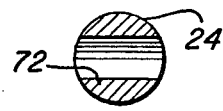
FIG. 4 is a sectional view taken on the line 4—4 of FIG. 1 and looking in the direction of the arrows.
Figure 5:
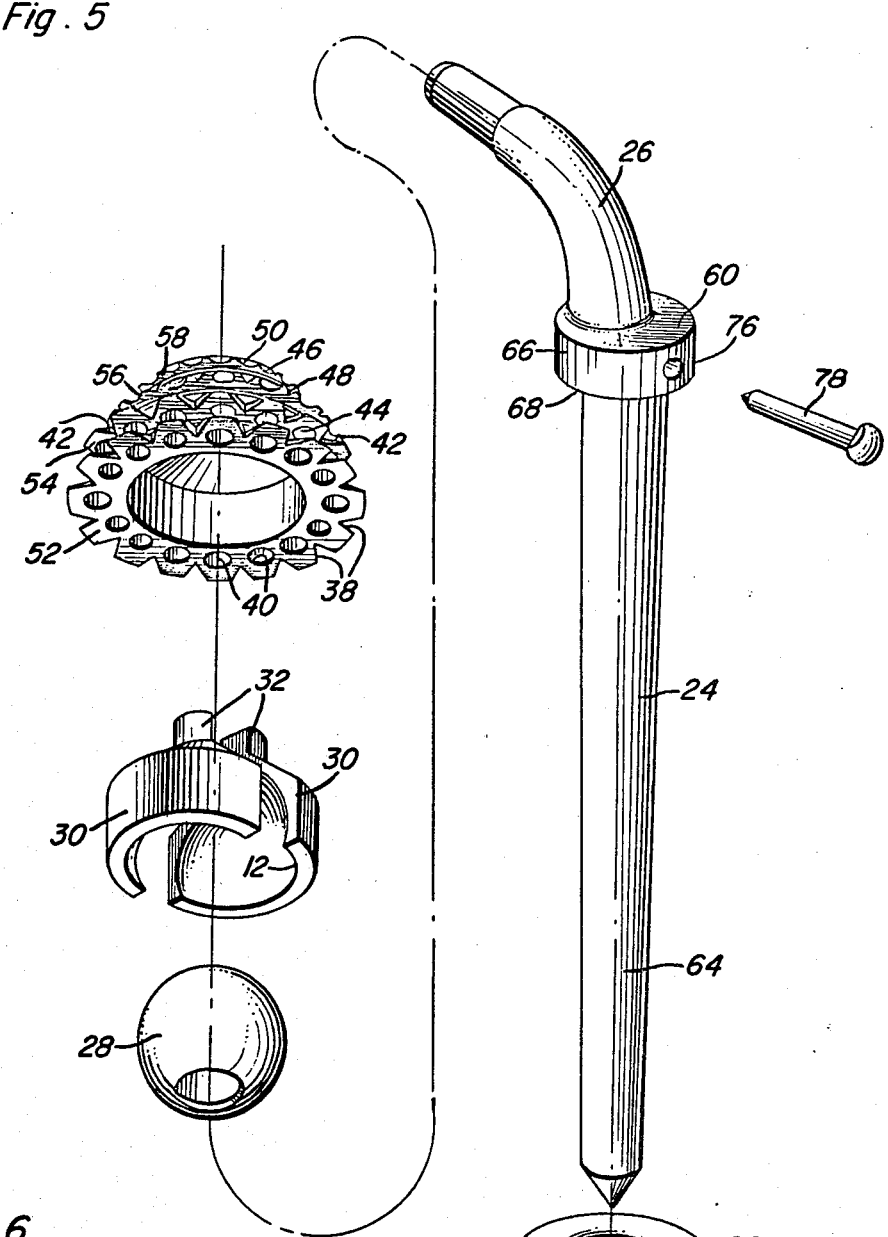
FIG. 5 is an exploded perspective view of the artificial hip.
Figure 6:
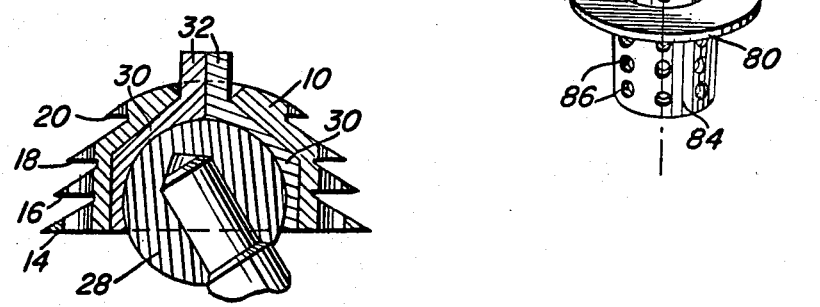
FIG. 6 is a fragmentary sectional view of a portion of the artificial hip illustrating the method of assembly.

With reference now to the drawings, wherein like reference characters designate like or corresponding parts throughout the several views, there is shown a machined acetabulum prosthesis 10 of the cotyloid cavity defining a socket 12 and having a plurality of blades 14, 16, 18, and 20 extending outwardly from the socket for engaging the prepared wall (not shown) of the cotyloid cavity.

A machined prosthesis 22 of the head of the femur is movably interconnected with acetabulum prosthesis 10 and includes a pin 24 to be driven into the bone-marrow channel of the femur (not shown), a curved neck 26 integral with pin 24 and a hip ball 28 fixedly positioned, e.g. by shrinking, on the neck and movably located within socket 12.

As here embodied, acetabulum prosthesis 10 includes two inserts 30, and each of the inserts has a surface area in contacting relationship with hip ball 28. The combined surface areas of the inserts contact hip ball 28 over a total of more than one-half the spherical surface area of the ball.

Each of inserts 30 includes a projection 32 that fits through an aperture 34 located in acetabulum prosthesis 10. In manufacturing the artificial hip joint, inserts 30 are positioned around hip ball 28, and projections 32 are then inserted through aperture 34. The projections are then hammered down or riveted and polished to be flush with the upper surface 36 of prosthesis 10.

The acetabulum prosthesis 10 preferably has four blades. The first blade 14 is the largest and extends around and exteriorly of socket 12. Blade 14 is preferably formed with a first plurality of notches 38 and with a first plurality of holes 40 alternately positioned with respect to notches 38. Second blade 16 also extends around and exteriorly of socket 12 and blade 16 has a second plurality of notches 42 and a second plurality of holes 44 alternately positioned with respect to notches 42.

Third blade 18 extends around exteriorly of socket 12 and is provided with a plurality of depressions 46 and with a third plurality of notches 48 alternately positioned with respect to the depressions. A fourth blade 20 is also provided and similarly extends around and exteriorly of socket 12. Blade 20 is provided with a pluraity of indentations 50, and holes 40 and 44, notches 38, 42, and 48 together with depressions 46 and indentations 50 assist in holding acetabulum prosthesis 10 in position within the hip and enable tissue and bone growth to extend through the holes to firmly affix prosthesis 10 in the desired position.

Each of blades 14, 16, 18 and 20 also defines a respective flat lower face 52, 54, 56, and 58, and each of these faces is positioned in parallel relationship with the others. This face configuration of the blades is important in enabling the blades to be embedded into the bone of the natural cotyloid cavity. Each of the notches is preferably formed to define an angle of substantially 30°, and it is by means of the bladed configuration of prosthesis 10 together with the apertures located in the blades that enable the prosthesis to be fixedly positioned within the prepared cotyloid cavity of the pelvis. The configuration of prosthesis 10 also permits the growth of bone tissue through the holes in the blades in such a way as to hold the prosthesis in position within the pelvis in a firm and lasting manner.

Prosthesis 22 of the head of the femur, in addition to pin 24 and neck 26, also preferably includes an enlarged shoulder 60 integral with and positioned between the pin and the neck, and the neck is preferably formed with a base 62 joined to the shoulder and eccentrically positioned with respect to the central axis 64 of the pin. Shoulder 60 defines a side portion 66 and a lower surface 68, and it is surface 68 that rests on the upper portion of the severed femur when the artificial hip joint is installed. In a preferred construction of the artificial hip joint, an innermost portion 70 of the neck also extends in a continuous manner from side portion 62 of the shoulder.

It is also preferable and the preferred embodiment illustrated provides for a curvature of neck 26 so as to form an angle of substantially 130° with pin axis 64. The angle is measured between the pin axis and an imaginary line passing from the pin axis through the center of hip ball 28 and tangentially to the innermost curved surface 70 of the neck.

Pin 24 also defines two slots 72 and 74 opening in directions parallel to the direction of curvature of neck 26. The function of these slots is similar to the function of the holes in prosthesis 10, and slots 72 and 74 permit bone tissue to grow therethrough so as to fix pin 24 and prosthesis 22 within the femur. Pin 24 is also tapered away from neck 26, and the neck is tapered away from the pin. The taper of the pin permits it to be driven downwardly and into the bonemarrow channel of the femur.

In an alternative arrangement and use of the artificial hip joint of this invention, shoulder 60 is provided with a hole 76 entering the side portion 66 of the shoulder. A rod 78 is also provided, and it is adapted to pass through a hole drilled in the greater trochanter (not shown) and to be driven into hole 76 to hold the greater trochanter in proper position after the artificial joint has been installed.

In another embodiment and use of the hip joint, a collar 80 is provided for insertion into the upper part of the femur and for providing additional support for the artificial hip on the femur when necessary. The collar is provided with a flange portion 82 for engaging the lower surface 68 of shoulder 60, and the collar is also provided with a sleeve portion 84 integral with flange portion 82 for sliding over pin 24 so that the collar can be positioned on the upper part of the severed femur. Pin 24 can, thus, be inserted through the collar and into the bone-marrow channel of the femur to cause shoulder 60 to rest on flange portion 82.

It is also preferable that sleeve portion 84 of the collar be provided with a plurality of holes 86 for enabling bone tissue to grow through the holes and to assist in holding the collar in its proper position on the femur.

Another important feature of this invention is the composition of the artificial hip joint and particularly the preferred use of cobalt alloy for the hip ball and for the inserts together with the use of titanium or a titanium alloy for the remaining portions of the joint. This combination of materials has proven to be highly effective in providing the desired strength for the hip joint while also providing for the desired resistance to corrosion. The use of cobalt alloy for the hip ball inserts does not result in galvanic action with the titanium or titanium alloy of the remainder of the joint, and the cobalt alloy provides the desired resistance to scoring necessary because of the frictional contact between the hip ball and the inserts. The metals or alloys utilized in forming the hip joint are preferably constituted of surgical grade materials.

In a preferred embodiment, both inserts 30 and hip ball 28 are comprised by weight of cobalt — 65%, chromium — 30%, and molybdenum — 5%. The remaining portions of the joint are preferably comprised of titanium alloy, and the titanium or a titanium alloy. The titanium is preferably a commercially pure metal having a 0.2% offset yield strength of 50,000 psi and sold under the tradename RMI 50 by Reactive Metals, Inc., Niles, Ohio. The titanium alloy preferably comprises by weight approximately 90% titanium, 6% aluminum, and 4% vanadium and is sold under the tradename RMI 6-Al-4V by Reactive Metals, Inc. Where collar 80 and rod 78 are utilized, these elements are also preferably comprised of the same titanium or titanium alloy that is used in the remaining portions of the joint.

Installation of the artificial hip joint of this invention may be accomplished by first baring the trochanter major by a straight lateral incision of the hip's outside surface. The trochanter major is then severed by a gouge and is moved upwardly together with the associated muscles. The hip bone or upper portion of the femur is then cut by a saw or gouge at the level of the lower edge of the trochanter minor. The head of the femur is then removed together with the neck and the intertrachanter region with the help of grooved gouges.

The bone-marrow channel of the femur is then worked by special conical milling cutters, the size of which is predetermined exactly with respect to the size of prosthesis pin 24. The bone-marrow channel of the femur is preferably reamed to a size that corresponds exactly to the size of pin 24. The natural cotyloid cavity is also worked with mushroom milling cutters, and the size of the biggest cutter should be 2–3 mm smaller in diameter than that of the outer dimensions of acetabulum prosthesis 10 of the cotyloid cavity. This is necessary to ensure a reliable attachment of prosthesis 10 to the bones of the pelvis.

After the natural cotyloid cavity of the pelvis has been properly prepared, prosthesis pin 24 is driven into the bone-marrow channel of the femur. One-half of acetabulum prosthesis 10 is then inserted into the prepared cotyloid cavity of the pelvis in such a way as to have blades 14, 16, 18, and 20 substantially perpendicular to the plane (not shown) joining the outside edges of the natural cotyloid cavity (not shown). Prosthesis 10 is then pressed into the natural cotyloid cavity with the help of a special tap and is gradually turned until the edges of largest blade 14 sink evenly 2-5 mm into the prepared natural cotyloid cavity walls. Prosthesis 10 cuts into the bones of the natural cotyloid cavity, and thereby ensures reliable attachment of prosthesis 10 to the bones making up the natural cotyloid cavity.

The previously severed trochanter major is then fastened by means of rod 78 to the outside surface of the upper end of the femur. A small hole 76 is provided in shoulder 60 of the prosthesis for this purpose and a hole is also drilled through the trochanter major so that rod 78 can pass through the hole in the trochanter major to be inserted into hole 76. The incision is then sutured together and postoperative procedures are then followed to avoid postoperative shock.

The holes provided in acetabulum prosthesis 10 and the slots provided in prosthesis 22 are intended for the growth of bone tissue into them as a result of the mechanical irritation of the bones caused by the operation, and such bone growth does occur to firmly hold the prostheses in position.

The present invention, thus, provides for an extremely strong and durable artificial hip joint that is highly resistive to corrosion and to other adverse actions within the human body. The joint is extremely versatile and is capable of performing all functions inherent in a normal human hip joint. The joint also advantageously relies on bone tissue growth stimulated by insertion of the artificial joint to strongly affix the prostheses of the joint in place.

The invention in its broader aspects is not limited to the specific details described, and departures may be made from such details without departing from the principles of the invention and without sacrificing its chief advantages.

What is claimed is:

1. An artificial hip joint comprising: an acetabulum prosthesis of the cotyloid cavity defining a chamber and including an insert positioned within the chamber for forming a socket; means for holding the insert in place in the chamber defined by the acetabulum prosthesis; and a prosthesis of the head of the femur movably interconnected with said acetabulum prosthesis and including a pin to be driven into the bone-marrow channel of the femur, a neck integral with the pin, and a hip ball fixedly positioned on the neck and movably mounted within said socket, the socket enveloping more than one-half of the hip ball to prevent withdrawal of the hip ball from the socket.

2. An artifical hip joint as in claim 1 wherein two said inserts are positioned within the chamber defined by the acetabulum prosthesis for forming the socket.

3. An artificial hip joint as in claim 2 wherein the acetabulum prosthesis has an aperture therein and the inserts each include means extending into said aperture for holding the inserts in place.

4. An artificial hip joint as in claim 3 wherein each of said means comprises a projection extending into said aperture for holding the inserts in position.

5. An artificial hip joint as in claim 4 wherein said projections extend through said aperture and are riveted to the acetabulum prosthesis.

6. An artificial hip joint as in claim 1, wherein said acetabulum prosthesis includes a plurality of blades extending outwardly away from the chamber for engaging the prepared wall of the cotyloid cavity.

* * * * *